(12) United States Patent
Benabid

(10) Patent No.: US 11,079,589 B2
(45) Date of Patent: Aug. 3, 2021

(54) OPTICAL FIBRE

(71) Applicants: CENTRE NATIONAL DE LA RECHERCHE SCIENTIFIQUE, Paris (FR); UNIVERSITE DE LIMOGES, Limoges (FR)

(72) Inventor: Abdel Fetah Benabid, Le Palais sur Vienne (FR)

(73) Assignees: CENTRE NATIONAL DE LA RECHERCHE SCIENTIFIQUE, Paris (FR); UNIVERSITE DE LIMOGES, Limoges (FR)

( * ) Notice: Subject to any disclaimer, the term of this patent is extended or adjusted under 35 U.S.C. 154(b) by 0 days.

(21) Appl. No.: 16/633,831

(22) PCT Filed: Jul. 11, 2018

(86) PCT No.: PCT/EP2018/068843
§ 371 (c)(1),
(2) Date: Jan. 24, 2020

(87) PCT Pub. No.: WO2019/020382
PCT Pub. Date: Jan. 31, 2019

(65) Prior Publication Data
US 2020/0241281 A1 Jul. 30, 2020

(30) Foreign Application Priority Data
Jul. 24, 2017 (FR) ........................ 1756993

(51) Int. Cl.
*G02B 6/02* (2006.01)
*G02B 23/24* (2006.01)
(Continued)

(52) U.S. Cl.
CPC .......... *G02B 23/2469* (2013.01); *A61B 1/043* (2013.01); *A61B 18/22* (2013.01);
(Continued)

(58) Field of Classification Search
CPC ................... A61B 2018/2227; G02B 6/02328
See application file for complete search history.

(56) References Cited

U.S. PATENT DOCUMENTS 7,340,140 B1 * 3/2008 Xu ..................... G02B 6/02323
385/125
2003/0231846 A1 * 12/2003 Fajardo .............. G02B 6/02357
385/125
(Continued)

OTHER PUBLICATIONS

Lombardini: "Nonlinear Optical Endoscopy With Micro-Structured Photonic Crystal Fibers," Optics.Physics.optics, Aix-Marselle Université, pp. 46, 50-57, 75-79, 105-109, 117-124, Dated Dec. 13, 2016.
(Continued)

*Primary Examiner* — Rhonda S Peace
(74) *Attorney, Agent, or Firm* — Greer, Burns & Crain, Ltd.

(57) ABSTRACT

An optical fibre for an ultrafast laser endoscope including at least the following structures: a hollow core, the periphery of which has an order of symmetry of at least six when considering axes of symmetry passing through the centre of the core and through the centre of convex shapes, seen from the centre of the core, the convex shapes at least partly making up the periphery of the core; an intermediate layer of cellular structure surrounding the core; a light conducting peripheral structure surrounding the intermediate layer of cellular structure; and an outer sheath surrounding the light-conducting peripheral structure. A particular advantage of the optical fibre is that it optimizes the emission of a high-power flux associated with fluorescence collection.

29 Claims, 5 Drawing Sheets

(51) Int. Cl.
    *A61B 1/04*     (2006.01)
    *A61B 18/22*    (2006.01)
    *A61B 18/00*    (2006.01)
(52) U.S. Cl.
    CPC ..... *G02B 6/02328* (2013.01); *G02B 6/02338* (2013.01); *A61B 2018/00577* (2013.01); *A61B 2018/2227* (2013.01)

(56) References Cited

U.S. PATENT DOCUMENTS

| | | | | |
|---|---|---|---|---|
| 2006/0083470 A1* | 4/2006 | Solarz | ............... | G02B 6/02328 385/125 |
| 2011/0038587 A1* | 2/2011 | Shaw | ................. | C03B 37/0122 385/127 |
| 2013/0022060 A1* | 1/2013 | Gaborel | ............... | G02B 6/4206 372/6 |
| 2016/0124144 A1 | 5/2016 | Benabid et al. | | |
| 2016/0317228 A1* | 11/2016 | Fermann | ................ | A61B 90/20 |
| 2020/0241281 A1* | 7/2020 | Benabid | ............. | A61B 1/00167 |

OTHER PUBLICATIONS

Benabid: "Hollow-Core Photonic Bandgap Fibre: New Light Guidance for New Science and Technology," Phil Trans. R. Soc. A, vol. 364, pp. 3439-3462, Dated Oct. 20, 2006.

Choi et al., "Improving Femtosecond Laser Pulse Delivery Through a Hollow Core Photonic Crystal Fiber for Temporally Focused Two-Photon Endomicroscopy," Scientific Reports, vol. 4, pp. 1-7, Dated Oct. 15, 2014.

Written Opinion from the corresponding French Patent Application No. 1756993, dated Jul. 24, 2017.

French Search Report from the corresponding French Patent Application No. 1756993, dated May 30, 2018.

International Search Report from the corresponding International Patent Application No. PCT/EP2018/068843, dated Oct. 4, 2018.

* cited by examiner

OPTICAL FIBRE

BACKGROUND

The invention relates to the field of optical fibres and in particular that of optical fibres for an ultrafast laser endoscope.

Endoscopy is a method for medical or industrial exploration or imaging which makes it possible in particular to view the interior of to channels or cavities that are inaccessible to the human eye. Conventionally, in medical endoscopy, the endoscope consists of an optical tube comprising an illumination coupled with a camera. An aim of endoscopy is to be able to carry out in situ imaging to be able to perform a diagnosis.

In certain, in particular medical, and more particularly surgical, applications, the endoscope can be coupled with a tool, for example a cutting tool or a tool suitable for another treatment of cellular tissues. The tool can be borne by the optical tube of the endoscope. The endoscope thus makes it possible to perform an in situ operation.

In the particular case of ablation of cells or specific tissues that are not able to be differentiated by eye or by standard medical imaging, endoscopy has a real advantage. In fact, the fluorescence of certain cells makes it possible to accurately detect an area to be removed. Fluorescence can be natural in certain cells or can be stimulated by applying a fluorescent product. As the fluorescence can be different according to the type of cell, it is possible to determine if an operation has or has not allowed the removal of a specific group of cells characterized by their fluorescence.

Excitation of the fluorescence can advantageously be carried out in situ by specific laser excitation. Ultrashort pulse lasers make it possible to generate fluorescence by two-photon excitation.

This fluorescence, and more specifically the associated microscopy, called two-photon or multiphoton microscopy, allows much higher resolutions than more conventional fluorescence microscopy systems. In fact, only the area where two photons recombine is capable of fluorescing; unlike single-photon fluorescence microscopy where all of the area passed through by the photon is capable of fluorescing. In contrast, two-photon microscopy is, a priori, an in vitro imaging instrument and thus cannot currently be transposed to an endoscopic instrument due to the dimension thereof.

On the other hand, the lasers called ultrashort pulse lasers, or ultrafast lasers, allow athermal ablation, i.e. without the propagation of energy in the form of heat in the surrounding tissues. Ultrashort pulse lasers are pulsed lasers with sub-picosecond temporal regimes producing high energy, for example between 0.5 and 0.35 joules.

Usually, the laser beams are routed in a free space. In order to avoid dispersion of the energy dispensed by the laser, it is possible to bring the laser source closer to the target via an articulated arm. However, such a device is particularly bulky and thus difficult to manipulate. This represents a problem in particular for fine positioning of the laser with respect to the area to be explored or to be operated on.

Solid optical fibres are simpler to use but they have a damage threshold that is too low with respect to the pulse energies emitted by the ultrafast lasers. In addition, their high dispersion and/or optical nonlinearity have the effect of distorting the temporal integrity of the pulse emitted.

Using Kagome-type fibres makes it possible to ensure a good radiant flux performance in addition to being flexible. A combination of a structure suitable for guiding an ultrashort pulse laser beam allowing in particular two-photon or multiphoton fluorescence excitation and a structure making it possible to collect a maximum of fluorescence would be particularly advantageous. However, the two types of guiding necessary have specific, even incompatible, structural constraints.

An aim of the invention is to propose an optical fibre making it possible both to convey a high power, low dispersion laser beam and to collect a luminous flux for example originating from a fluorescence.

SUMMARY

To this end, the present invention proposes an optical fibre comprising at least the following structures:

a hollow core the periphery of which has an order of symmetry of at least six when considering axes of symmetry passing through the centre of the core and through the centre of convex shapes, seen from the centre of the core, said convex shapes at least partially composing the periphery of the core;

an intermediate layer having a cellular structure surrounding the core;

a light-conducting peripheral structure surrounding the intermediate layer having a cellular structure;

an external cladding surrounding the light-conducting peripheral structure.

The intermediate layer having a cellular structure can have a thickness comprised between 10 μm and 75 μm.

Preferentially, the intermediate layer having a cellular structure has walls the thickness of which is comprised between 100 nm and 2000 nm.

The light-conducting peripheral structure has for example a thickness comprised between 1 μm and 10 μm.

The minimum radius of the periphery of the core can advantageously be comprised between 20 μm and 60 μm, advantageously it can be comprised between 30 μm and 50 μm.

The refractive index of the external cladding is preferably comprised between 1.43 and 1.47 for at least one wavelength $\lambda_c$ comprised for example between 300 nm and 3 μm or even in the infrared domain between 800 nm and 3 μm. Preferentially, for a wavelength of 1 μm, the refractive index of the external cladding is 1.45.

The core can have a refractive index of the order of 1, to the nearest $1/100^{th}$ for wavelengths $\lambda_c$ comprised for example between 300 nm and 3 μm or even in the infrared domain between 800 nm and 3 μm. Preferably, the refractive index of the core can be 1 for a wavelength of 1 μm.

The core is preferably in particular filled with a gas, which can be air.

The thickness of the external cladding can be comprised between 30 μm and 410 μm. Advantageously, the thickness of the external cladding can be comprised between 80 μm and 280 μm.

The external cladding can be composed of silica.

The light-conducting peripheral structure can have a refractive index greater than that of the external cladding for at least one wavelength comprised for example between 300 nm and 3 μm or even in the infrared domain between 800 nm and 3 μm. Preferentially, the refractive index of the light-conducting peripheral structure can be 1.5 for a wavelength of 1 μm.

The light-conducting peripheral structure has for example a numerical aperture greater than 0.1 for at least one wavelength comprised for example between 300 nm and 3

µm or even in the infrared domain between 800 nm and 3 µm. Preferentially, the numerical aperture can be comprised between 0.1 and 0.5 for at least one wavelength comprised for example between 300 nm and 2 µm or even in the infrared domain between 800 nm and 3 µm, and advantageously, it can be approximately 0.15 for a wavelength comprised between 300 nm and 800 nm.

The light-conducting peripheral structure can be composed of germanium-doped silica.

At least one of the structures of the optical fibre can comprise walls or bridges of a thickness comprised between 100 nm and 2000 nm. Preferentially, the thickness of the bridges of certain embodiments can be comprised between 200 nm and 700 nm and advantageously, it can be approximately 700 nm. The thickness of the bridges is of a dimension less than the wavelength to be guided, to limit unwanted coupling phenomena.

The bridges can be bridges made from glass or silica.

In certain particular embodiments, the light-conducting peripheral structure can be a continuous annular peripheral structure having a thickness comprised between 2 µm and 8 µm and advantageously approximately 3 µm.

In certain embodiments, the periphery of the core can have a shape to resulting from a combination of convex elliptical arcs seen from the centre of the core. This structure allows better energy confinement in the core of the fibre and thus a lower optical mode overlap with the light-conducting peripheral structure.

The elliptical arcs are thus for example parameterized by a coefficient $b=d/r$, where d is a first radius of the ellipse directed towards the centre of the core and r is a second radius of the ellipse substantially perpendicular to d, b being comprised between 0.4 µm and 1.5 µm.

The combination of elliptical arcs can comprise alternately a first elliptical arc the smallest distance to the centre of the core of which is a radius $R_{in}$, and a second elliptical arc the smallest distance to the centre of the core of which is a radius $R_{out}$, with $R_{in}/R_{out}$ comprised between 0.6 and 0.9.

The coefficient b of the first elliptical arc can be 0.8, the coefficient b' of the second elliptical arc can be 0.5, and $R_{in}/R_{out}$ can then be comprised between 0.6 and 0.9 and preferentially close to 0.8.

The cellular structure can be a Kagome structure. The combination of elliptical arcs constitutes a continuous boundary between the Kagome structure and the core.

The Kagome structure has for example a thickness corresponding to at least one Kagome structure element having a diameter that can be comprised between 10 µm and 25 µm.

The Kagome structure can advantageously have a thickness comprised between one and four Kagome structure elements and preferentially between two and three Kagome structure elements.

The core of a fibre having a Kagome structure can have a numerical aperture less than 0.05 and preferentially between 0.005 and 0.05. Advantageously, the numerical aperture of the core of an optical fibre having a Kagome structure can be of the order of 0.01.

The optical mode overlap of the Kagome structure is for example less than $10^{-4}$ and preferentially less than $10^{-6}$.

Each element of the Kagome structure can be delimited by an assembly of bridges. This bridge architecture defines the Kagome structure.

The bridges of the Kagome structure have for example a refractive index less than that of the external cladding or substantially equal to that of the external cladding to plus or minus 10%. Advantageously, the refractive index of the bridges of the Kagome structure can be equal to 1.45 for a wavelength of 1 µm.

The bridges of the Kagome structure have for example a thickness comprised between $\mu_c/2.6$ and $\lambda_c/2.8$, $\lambda_c$, being a wavelength to be guided.

The space between the bridges of the Kagome structure can be filled with a gas, preferentially air, having a pressure preferably comprised between 10 mbar and 1 bar.

In a first particular embodiment, the optical fibre can comprise a Kagome structure. In the context of this first embodiment, the light-conducting peripheral structure can comprise blocks situated between the Kagome structure and the external cladding. For example the blocks can be situated in the interstices between the Kagome structure and the external periphery having the Kagome structure.

The blocks have for example a thickness greater than the thickness of the bridges of the Kagome structure. Preferentially, the thickness of the blocks can be comprised between 1 µm and 10 µm, and even more preferentially between 2 µm and 4 µm. A thickness of the order of 2.5 µm is particularly advantageous.

The blocks have for example a refractive index greater than that of the external cladding and preferentially of the order of 1.5 for a wavelength of 1 µm.

The blocks can be produced from germanium-doped silica.

In certain embodiments, the optical fibre can comprise between the external cladding and the light-conducting peripheral structure, a gas cladding having an annular structure, supported by bridges extending radially from the exterior of said optical fibre in the direction of the centre of the optical fibre.

Preferentially, the bridges of the gas cladding have a thickness comprised between 100 nm and 2000 nm.

The gas cladding has a thickness which can be comprised between 10 µm and 100 µm, and preferentially between 20 µm and 60 µm. In a particularly advantageous embodiment, the thickness of the gas cladding can be of the order of 30 µm.

The gas cladding can be preferentially filled with air having a refractive index 1 for a wavelength of 1 µm.

Advantageously, the gas contained in the gas cladding can have a pressure and a composition identical to the gas situated in the cellular structure.

The bridges of the gas cladding can have a thickness of the order of 700 nm; the thickness of the bridges of the gas cladding preferentially has a dimension less than the wavelength to be guided, to limit unwanted coupling phenomena.

The bridges of the gas cladding have for example a refractive index of 1.45 to 1.5 for a wavelength of 1 µm.

In a second particular embodiment, the Kagome structure can be in contact with the light-conducting peripheral structure, itself in contact with the external cladding.

In a third particular embodiment, the Kagome structure can be in contact with the light-conducting peripheral structure, itself in contact with the gas cladding which can itself be in contact with the external cladding.

In several embodiments, the optical fibre can further comprise an internal cladding between the intermediate layer having a cellular structure and the light-conducting peripheral structure. The internal cladding can thus be in contact with the intermediate layer having a cellular structure.

The internal cladding can have a thickness comprised between 100 nm and 800 nm and preferentially of the order of 4 µm.

The refractive index of the internal cladding can be 1.45 for a wavelength of 1 μm.

The internal cladding is for example made from the same material as the external cladding.

In a fourth particular embodiment, the internal cladding can be in contact with the light-conducting peripheral structure. Said light-conducting peripheral structure can thus be in contact with the external cladding. In this embodiment, the refractive index of the light-conducting peripheral structure can be greater than the refractive index of the internal cladding.

In several alternative embodiments, the intermediate layer having a cellular structure can comprise hollow cylinders at a distance from one another, having for example a refractive index of 1.45 for a wavelength of 1 μm.

The hollow cylinders have for example an external diameter comprised between 10 μm and 25 μm, and preferentially for example of the order of 18 μm.

The walls of the hollow cylinders can have a thickness comprised between 100 nm and 2000 nm. The thickness of the walls of the cylinders has a dimension less than the wavelength to be guided, in order to limit unwanted coupling phenomena.

The walls of the hollow cylinders are for example made from silica.

The intermediate layer having a cellular structure can advantageously comprise a single layer of hollow cylinders preferably made from a dielectric material, for example silica.

The hollow cylinders are for example at a distance from one another, the interval between two hollow cylinders is for example of the order of 800 nm.

In a fifth particular embodiment, each hollow cylinder can be in contact with the light-conducting peripheral structure.

In a sixth particular embodiment, each hollow cylinder can be in contact with the internal cladding.

The internal cladding has for example the same refractive index as the external cladding plus or minus 10%.

In a seventh particular embodiment, the hollow cylinders can be in contact with the light-conducting peripheral structure, itself in contact with the gas cladding. Said gas cladding can be directly in contact with the external cladding.

Advantageously, the dimensions and characteristics of the different embodiments of the optical fibre according to the invention make it possible both to maximize the high-power flux and to maximize the collection of fluorescence. The invention thus optimizes the emission of a high-power flux associated with a collection of fluorescence.

Another advantage of an optical fibre according to the invention is to make it possible to allow the high-power treatment laser beam to be routed in a secure, flexible and practical manner.

BRIEF DESCRIPTION OF THE DRAWINGS

Other advantages and characteristics of the invention will become apparent on reading the detailed description of several embodiments that are in no way limitative, and from the attached drawings, in which.

Figure 1:
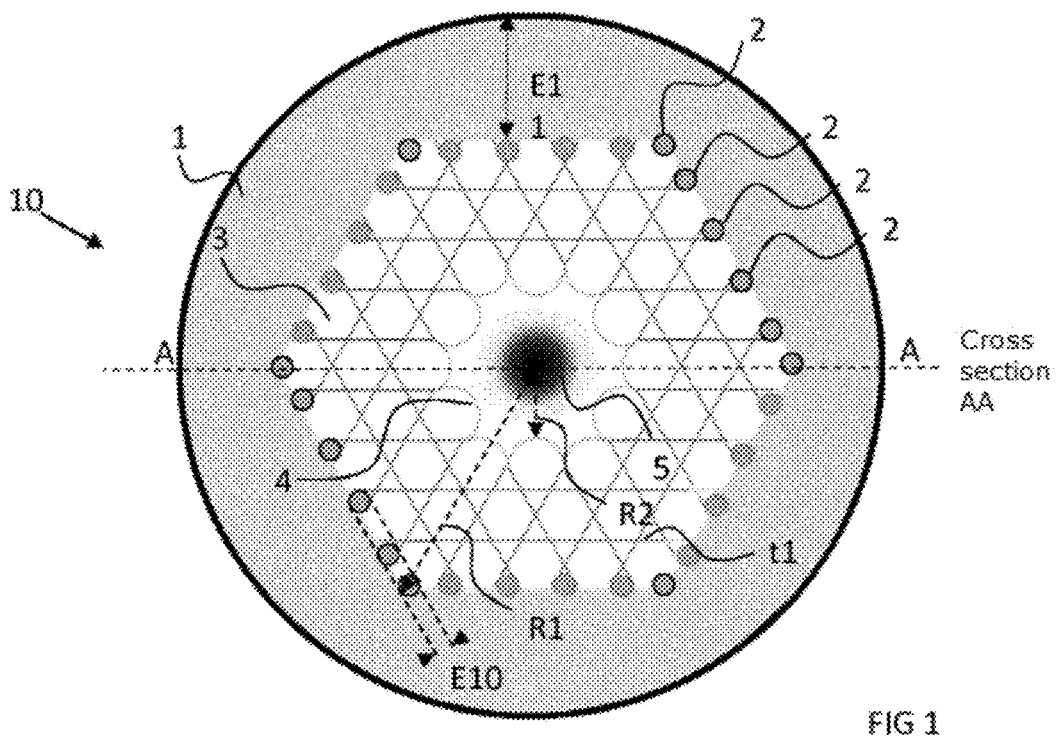
FIG. 1 represents a first embodiment of the optical fibre according to the invention.

As these embodiments are in no way limitative, variants of the invention can be considered in particular comprising only a selection of the characteristics described or illustrated hereinafter, in isolation from the other characteristics described or illustrated (even if this selection is isolated within a phrase comprising these other characteristics), if this selection of characteristics is sufficient to confer a technical advantage or to differentiate the invention with respect to the state of the prior art. This selection comprises at least one, preferably functional, characteristic without structural details, and/or with only a part of the structural details if this part alone is sufficient to confer a technical advantage or to differentiate the invention with respect to the state of the prior art.

DETAILED DESCRIPTION

The invention is incorporated into an endoscope allowing both a fluorescent medical imaging by laser excitation and a cellular ablation by athermal laser ablation, all in a compact element. Advantageously, these two functions are borne by one and the same optical fibre. This optical fibre has the feature of allowing guiding by an inhibited coupling mechanism and by a total internal reflection mechanism, also called TIR. Guiding by inhibited coupling, IC, is based on a significant reduction in the guided mode optical integral in the core of the fibre and cladding modes. Unlike guiding by TIR or by band gap, guiding by IC does not require total absence of cladding modes at the effective index and guide frequency. In fact, the guided mode in the fibres guiding by IC is based on a reduction in its spatial overlap with the silica of the cladding and on a significant asymmetry of the transverse component between the field of the core and that of the cladding. In algebraic terms, the field state of the core mode $|\varphi_{core}>$ and that of the cladding modes $|\varphi_{clad}>$ show a scalar product (i.e. $<\varphi_{clad}|\Delta n|\varphi_{core}>$) tending towards zero. The more this scalar product decreases, the better the transmission of the fibre. In the context of the present invention, $\Delta n$ is the transverse profile of the index of the structure of the cladding. Consequently, guiding by IC follows physical principles and requires design rules that are completely different to those which govern guiding by TIR or band gap in the fibres.

Inhibited guiding thus makes it possible to guide a laser beam having a high power and a very short pulse length. As for guiding by total internal reflection, this makes it possible to collect fluorescence. This type of optical fibre is called active double-clad optical fibre.

The optical fibre that is the subject of the invention is described firstly, by specifying the characteristics common to the different embodiments with reference to FIGS. 1, 2, 3, 4, 5, 6 and 7, then the characteristics specific to each embodiment shown on each FIGS. 1, 2, 3, 4, 5, 6, and 7. Characteristics Common to FIGS. 1, 2, 3, 4, 5, 6 and 7

With reference to FIGS. 1, 2, 3, 4, 5, 6, 7, the optical fibre 10, 20, 35, 45, 54, 65, 75 according to the invention comprises at least the following structures:

a hollow core 5, 25, 33, 44, 52, 64, 74 the periphery 4 of which, represented in FIG. 1, has an order of symmetry of at least six when considering axes of symmetry passing through the centre of the core 5, 25, 33, 44, 52, 64, 74 and through the centre of convex shapes seen from the centre of the core, said convex shapes at least partially composing the periphery 4 of the core;

an intermediate layer having a cellular structure 3, 24, 32, 43, 53, 63, 73 surrounding the core 5, 25, 33, 44, 52, 64, 74;

a light-conducting peripheral structure 2, 21, 31, 41, 51, 61, 72 surrounding the intermediate layer having a cellular structure;

an external cladding 1, 23, 30, 40, 50, 60, 70 surrounding the light-conducting peripheral structure.

The order of symmetry of the hollow core 5, 25, 33, 44, 52, 64, 74 is the number of axes of symmetry of the periphery 4, each of these axes passing:

necessarily through the centre of the core 5, 25, 33, 44, 52, 64, 74 and preferably through the centre of one of the convex shapes (seen from the centre of the core) at least partly composing the periphery 4. By hollow core 5, 25, 33, 44, 52, 64, 74 is meant a core of the optical fibre having a cylindrical shape filled with a gas. The periphery 4 of the core is the external delimitation of the core within the optical fibre. The periphery 4 of the core has at least six symmetries in its pattern. The symmetries have as axis of symmetry six straight lines passing through the centre of the core 5, 25, 33, 44, 52, 64, 74. The periphery 4 of the core comprises an assembly of convex shapes, or negative curves seen from the centre of the core 5, 25, 33, 44, 52, 64, 74. Such shapes advantageously make it possible to increase the absence of optical mode overlap of the light-conducting peripheral structure 2, 21, 31, 41, 51, 61, 72 with respect to the core 5, 25, 33, 44, 52, 64, 74. The centre of the core 5, 25, 33, 44, 52, 64, 74 is also the centre of the optical fibre 10, 20, 35, 45, 54, 65, 75.

The hollow core 5, 25, 33, 44, 52, 64, 74 allows a high-energy laser to be guided by inhibited coupling, which makes it possible to guide a very high-powered laser very accurately. The high-energy laser also allows fluorescence excitation of the illuminated tissues.

The light-conducting peripheral structure 2, 21, 31, 41, 51, 61, 72 makes it possible to collect the fluorescence provoked by the laser pulse guided by inhibited coupling in the hollow core, using total internal reflection. The optical fibre is then called "double-clad" and thus allows the return and reading of the fluorescence information from the tissues. This method makes it possible in particular to recognize the tissue onto which the laser pulse must be directed, but also to verify that all of a cell or a group of cells has been removed, for example.

For each structure or layer, except bridges t1 to t9 introduced below, by "thickness" is meant throughout the present description a distance between:

the internal radius of said structure or layer of the optical fibre, i.e. the smallest circle, centred on the centre of the core 5, 25, 33, 44, 52, 64, 74, and passing through at least one point of said structure or layer, and the external radius of said structure or layer, i.e. the largest circle, centred on the centre of the core 5, 25, 33, 44, 52, 64, 74, and passing through at least one point of said structure or layer.

The intermediate layer 3, 24, 32, 43, 53, 63, 73 having a cellular structure preferentially has a thickness comprised between 10 µm and 75 µm. In order to ensure guiding by inhibited coupling in the core of the fibre of a high power pulse without deformation of the pulse, without loss of power and without risk of decoupling in the other parts of the optical fibre, the thickness of the intermediate layer having a cellular structure must be at least 10 µm.

Above the thickness of 75 µm, there is no substantial benefit for the inhibited coupling, in other words, the optical mode overlap between the core and the light-conducting peripheral structure is substantially the same. In addition, adding thickness compromises the collection of light by total internal reflection by the light-conducting peripheral structure. In fact, the light-conducting peripheral structure must be as close as possible to the laser excitation pulse in order to collect a maximum of fluorescence.

The light-conducting peripheral structure 2, 21, 31, 41, 51, 61, 72 has a thickness E10, E22, E31, E41, E51, E61, E72 comprised between 1 µm and 10 µm.

In all of the description, by "radius" is meant a distance between the centre of the optical fibre and a given point of a structure of the optical fibre according to the invention.

A minimum radius of the periphery 4 of the core R2, R20, R30, R40, R50, R60, R70 is comprised between 20 µm and 60 µm, advantageously, it can be comprised between 30 µm and 50 µm.

In general, the optical fibre according to the invention is arranged in order to guide light at a reference wavelength (also called wavelength to be guided) comprised within the infrared domain between 800 nm and 3 µm.

A refractive index of the external cladding 1, 23, 30, 40, 50, 60, 70 is comprised between 1.43 and 1.47 for at least one wavelength $\lambda_c$ comprised for example between 300 nm and 3 µm or even in the infrared domain between 800 nm and 3 µm; and preferentially, for a wavelength of 1 µm, the refractive index of the external cladding is 1.45.

The core 5, 25, 33, 44, 52, 64, 74 can have a refractive index of the order of approximately 1 to the nearest $\frac{1}{100}^{th}$ for at least one wavelength comprised for example between 300 nm and 3 µm or even in the infrared domain between 800 nm and 3 µm; and preferably 1 for a wavelength of 1 µm.

The core 5, 25, 33, 44, 52, 64, 74 is filled with a gas which can be air. Advantageously, it is possible to guide a pulse having a very short duration in the core owing to a very low dispersion and a management of the gas inside the core, in particular its pressure. The pressure value of the gas inside the core is of the order of 1 µBar to 10 Bar and preferentially of the order of 1 mBar to 1 Bar.

A thickness E11, E20, E30, E40, E50, E60, E70 of the external cladding 1, 23, 30, 40, 50, 60, 70 is comprised between 30 µm and 410 µm. Advantageously, the thickness of the external cladding can be comprised between 80 µm and 280 µm.

The external cladding 1, 23, 30, 40, 50, 60, 70 is for example composed of silica.

The light-conducting peripheral structure 2, 21, 31, 41, 51, 61, 72 has a refractive index greater than that of the external cladding 1, 23, 30, 40, 50, 60, 70 for the at least one wavelength comprised for example between 300 nm and 3 µm or even in the infrared domain between 800 nm and 3 µm, and preferentially 1.5 for a wavelength of 1 µm.

The light-conducting peripheral structure 2, 21, 31, 41, 51, 61, 72 has a numerical aperture greater than 0.1 for the at least one wavelength comprised for example between 300 nm and 3 µm or even in the infrared domain between 800 nm and 3 µm. Preferentially, the numerical aperture of the light-conducting peripheral structure is comprised between 0.1 and 0.5 for the at least one wavelength comprised between 400 nm and 2 µm. In the methods for manufacturing the optical fibre according to the invention, the target numerical aperture is 0.15 for a wavelength comprised between 300 nm and 800 nm.

The light-conducting peripheral structure 2, 21, 31, 41, 51, 61, 72 can be composed of germanium-doped silica.

With reference to the embodiments shown in FIGS. 1, 2, 3, 4, 5, 6, 7, at least one of the structures of the optical fibre comprises walls or bridges t1, t2, t3, t4, t5, t6, t7, t8, t9. The walls or bridges t1, t2, t3, t4, t5, t6, t7, t8, t9 have a thickness t comprised between 100 nm and 2000 nm. Thus the cellular structure has walls of a thickness t comprised between 100 nm and 2000 nm.

The thickness of the walls or bridges t1, t2, t3, t4, t5, t6, t7, t8, or t9 is defined as the smallest dimension passing through a bridge, perpendicular to a local direction of elongation of said bridge. The thickness of the walls or bridges can advantageously have a dimension less than the length of the guided wavelength, in order to limit unwanted coupling phenomena.

The bridges can be bridges made from glass or silica, or from germanium-doped silica.

These bridges are spaced apart by a gas, preferably air.

Preferentially, for the embodiments shown in FIGS. 1, 2, 3, 4, 7, the thickness t of the glass bridges can be comprised between 200 nm and 700 nm and advantageously it can be approximately 700 nm. The thickness t of the glass bridges is linked to the wavelength of the laser as well as to the refractive index of the glass bridges. This relationship is clarified below.

The hollow core 5, 25, 33, 44, 52, 64, 74 has a numerical aperture NA1, for the at least one wavelength $\lambda_c$ comprised for example between 300 nm and 3 μm and even in the infrared domain between 800 nm and 3 μm, less than 0.05 and preferentially comprised between 0.005 and 0.05.

The light-conducting peripheral structure 2, 21, 31, 41, 51, 61, 72 has:

a numerical aperture NA2 in the case of a continuous light-conducting peripheral structure 2, or several numerical apertures NA2, NA3, NA4, etc. in the case of a discontinuous light-conducting peripheral structure 2, for example formed by several blocks as in the case shown in FIG. 1, for the at least one wavelength A comprised for example between 300 nm and 3 μm or even in the infrared domain between 800 nm and 3 μm. The numerical aperture of the light-conducting peripheral structure is at least ten times greater than the numerical aperture NA1 of the hollow core 5, 25, 33, 44, 52, 64, 74 and/or preferably greater than 0.1.

The intermediate layer having a cellular structure 3, 24, 32, 43, 53, 63, 73 comprises walls or bridges t1, t3, t5, t6, t4, t8, t9 each delimiting cells, typically cells with Kagome structure or hollow cylinders. The walls or bridges t1, t3, t5, t6, t4, t8, t9 are made from a material having a refractive index comprised between 1.43 and 1.47 for the at least one wavelength $\lambda_c$ comprised for example between 300 nm and 3 μm or even in the infrared domain between 800 nm and 3 μm. Said material is for example silica.

Each cell is filled with a gas:

having a refractive index comprised between 1 and 1.1 for the at least one wavelength A comprised for example between 300 nm and 3 μm or even in the infrared domain between 800 nm and 3 μm (for example consisting of or comprising air), and/or having a pressure less than 10 Bar and/or greater than 1 μBar. The pressure of the gas inside each cell is determined as a function of a compromise between a reduction of pressure to remove nonlinear effects in the propagation and a use of said nonlinear effects to further compress the pulse.

Characteristics Common to FIGS. 2, 3, 4, 5, 6 and 7

In the embodiments shown in FIGS. 2, 3, 4, 5, 6, 7, the light-conducting peripheral structure 21, 31, 41, 51, 61, 72 is a continuous annular peripheral structure having a thickness E22, E31, E41, E51, E61, E72, comprised between 2 μm and 8 μm, and preferentially approximately to 3 μm. The light-conducting peripheral structure makes it possible to collect the fluorescence emitted by a body using total internal reflection to convey this light.

Characteristics Common to FIGS. 1, 2, 3, and 4

In the embodiments represented in FIGS. 1, 2, 3, 4, the periphery 4 of the core 5, 25, 33, 44 can have a shape resulting from a combination of convex elliptical arcs seen from the centre of the core. In other words, the periphery of the core is formed from an assembly of curves having a negative curvature seen from the centre of the core.

Figure 8:
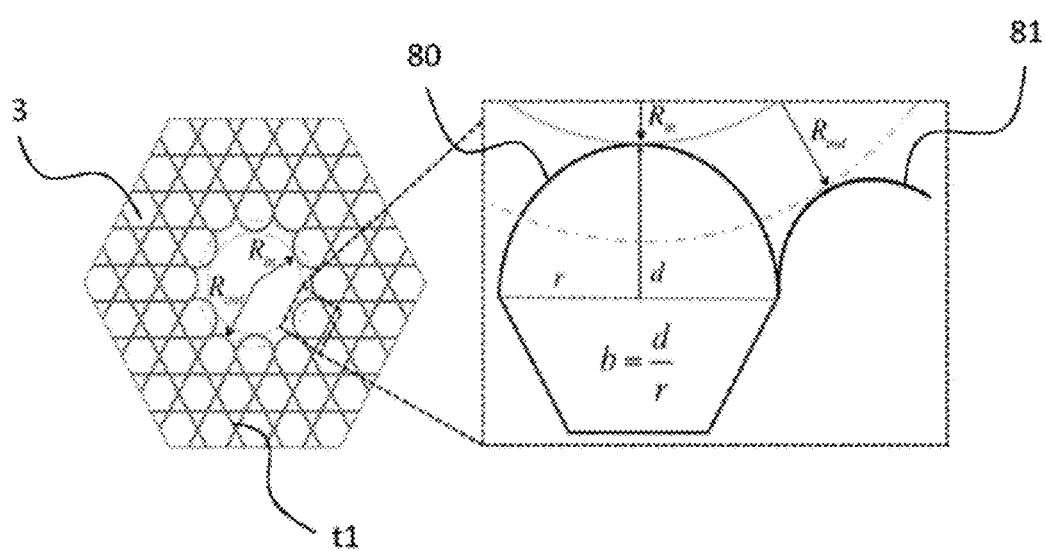
FIG. 8 represents a Kagome structure.

As represented in FIG. 8, the elliptical arcs 80, 81 are parameterized by a coefficient b=d/r, where d is a first radius of ellipse borne by an axis passing through the centre of the core 5, 25, 33, 44 and r is a second radius of ellipse passing through an axis substantially perpendicular to d, b being comprised between 0.4 μm and 1.5 μm.

The combination of elliptical arcs can comprise alternating at least two, and preferably exactly two types of elliptical arc:

a first type of elliptical arc 80, the smallest distance to the centre of the core of which is a radius $R_{in}$, and a second type of elliptical arc 81, the smallest distance to the centre of the core of which is a radius $R_{out}$, with $R_{in}/R_{out}$ less than 1 and for example comprised between 0.6 and 0.9.

The coefficient b=b1 of the first type of elliptical arc 80 can be 0.8, the coefficient b=b2 of the second elliptical arc 81 can be 0.5. $R_{in}/R_{out}$ can then be comprised between 0.6 and 0.9 and preferentially close to 0.8.

The cellular structure can be a Kagome structure 3, 24, 32, 43, the combination of elliptical arcs then constitutes a continuous boundary between the Kagome structure 3, 24, 32, 43 and the core 5, 25, 33, 44. The presence of this boundary between the Kagome structure and the core makes it possible to limit the number of unitary elements for producing the confinement of the radiation in the core and thus advantageously limits the thickness of the Kagome structure 3, 24, 32, 43. Each arc of the boundary can form one or more sides of the first elements of the Kagome structure starting from the core.

Structures of Kagome type are particularly indicated for guiding by internal coupling as they ensure a very good energy flux performance, i.e. physical resistance before breakdown of the fibre. Fibres of Kagome type are hollow fibres having a microstructured cross-section. The feature of this type of fibres is to provide an empty fibre core and a type of guiding making it possible both to propagate the light while limiting losses and to guide very short laser pulses without deteriorating its temporal and spectral structure, thus enabling a very good flux performance. This type of fibre allows a transfer of high-power light pulses and in particular ultrashort pulses of the femtosecond type. The femtosecond laser allows athermal ablation of a material or a tissue. It is thus possible for example to remove a cancerous tissue without damaging the neighbouring healthy tissues.

The Kagome structure 3, 24, 32, 43 has a thickness corresponding to at least one element, or cell, having Kagome structure with a diameter comprised between 10 μm and 25 μm. Below this minimum thickness, the optical mode overlap is greater and thus the risk of decoupling in the other parts of the fibre is high. There is in this case a risk of destruction of the optical fibre.

The Kagome structure 3, 24, 32, 43 can advantageously have a thickness comprised between one and four elements, or cells, having a Kagome structure, preferably between two and three elements, or cells having a Kagome structure. Above a thickness corresponding to three elements, the light-conducting peripheral structure 2, 21, 31, 41 is too far away from the core. Now, the light-conducting peripheral structure 2, 21, 31, 41 allows the collection of the fluorescence from the tissues, said fluorescence being able to be induced by the laser pulses originating from the core of the fibre. The light-conducting peripheral structure 2, 21, 31, 41 must thus be as close as possible to the core of the fibre in order to allow a collection of fluorescence that is sufficient to be able to distinguish the fluorescent cells from the non-fluorescent cells for example.

In FIGS. 1, 2, 3, 4, the Kagome structures are situated between a first minimum radius R2, R20, R30, R40 starting from the centre of the optical fibre 10, 20, 35, 45 and a second maximum radius R1, R21, R31, R41 starting from the centre of the optical fibre 10, 20, 35, 45.

The core of an optical fibre having a Kagome structure has a to numerical aperture less than 0.05 and preferentially between 0.005 and 0.05. Advantageously, the numerical aperture of the core of an optical fibre having a Kagome structure can be of the order of 0.01.

The optical mode overlap of the Kagome structure is less than $10^{-4}$ and preferentially less than $10^{-6}$. This overlap ensures very low transmission losses in the guiding of the ultra-energetic pulses.

Each element, or cell, of the Kagome structure is delimited by an assembly of glass bridges t1, t3, t5, t6. Each element having the Kagome structure is for example a six-sided parallelogram. The bridges constituting these sides can be continuous though the Kagome structure so as to form different sides of different cells of the Kagome structure, these different sides being arranged on one and the same line.

The glass bridges of the Kagome structure can have a refractive index less than that of the external cladding or substantially equal to that of the external cladding plus or minus 10%. Advantageously, the refractive index can be equal to 1.45 for a wavelength of 1 µm.

The glass bridges of the Kagome structure have a thickness t comprised between $\lambda_c/2.6$ and $\lambda_c/2.8$, $\lambda_c$ being a wavelength to be guided.

The wavelength to be guided is comprised within the following interval:

$$\lambda_c \in \left[ t\sqrt{n_g^2-1}\,\frac{2m+3}{m(m+1)},\, \frac{2}{3}t\sqrt{n_g^2-1}\,\frac{3m+4}{m(m+1)} \right]$$

where m is a positive integer, $n_g$ is the refractive index of the glass bridges and t the thickness of the glass bridges. Preferably, m is chosen equal to one. And thus $\lambda_c$ can be approximated by $$\lambda_c \approx \frac{5t}{2}\sqrt{n_g^2-1}$$

Typically, for a refractive index of 1.45, the thickness t is thus comprised between $\lambda_c/2.6$ and $\lambda_c/2.8$. For example, for a laser emitting for example at $\lambda_c=1030$ nm, t is comprised between 392 nm and 368 nm.

The space between the glass bridges of the Kagome structure is filled with a gas, preferentially air, having a controllable pressure comprised between 10 mbar and 1 bar.

Characteristics Specific to FIG. 1

In the first embodiment diagrammatically illustrated in FIG. 1, the first optical fibre 10 comprises a Kagome structure 3 as defined above. The light-conducting peripheral structure comprises blocks 2 situated between the Kagome structure 3 and the external cladding 1. Said blocks can be situated in the interstices having the Kagome structure 3 at the external periphery of the Kagome structure 3 with respect to the core 5. The blocks 2 are thus arranged in interstices of the Kagome structure 3 to facilitate manufacture. The number of blocks 2 is thus correlated with the number of interstices between the external cladding 1 and the Kagome structure 3. The external cladding 1 is for example directly in contact with the blocks 2 and the Kagome structure 3. In FIG. 1, and by way of example, the blocks 2 are positioned on the ridges and the vertices of a hexagon. Other configurations of the blocks 2 can be used depending on manufacturing constraints. The distance of the blocks 2 from the core 5 is comprised between 10 µm and 100 µm and preferentially between 10 µm and 75 µm. This distance advantageously makes it possible to avoid couplings with the propagation mode of the core 5.

The blocks 2 have a thickness E10 greater than the thickness t of the glass bridges t1 of the Kagome structure 3. Preferentially, the thickness E10 of the blocks can be comprised between 1 µm and 10 µm, and even more preferentially between 2 µm and 4 µm. A thickness E10 of the order of 2.5 µm is particularly advantageous.

The blocks 2 have a refractive index greater than that of the external cladding 1 and preferentially of the order of 1.5 for a wavelength of 1 µm. Advantageously, the numerical aperture of the blocks 2 is greater than the index difference between the blocks 2 and the external cladding 1. The refractive index of the blocks 2 is substantially close to the refractive index of the Kagome structure 3 to avoid couplings with the propagation mode of the core 5.

The blocks can be produced for example from germanium-doped silica.

Figure 2:
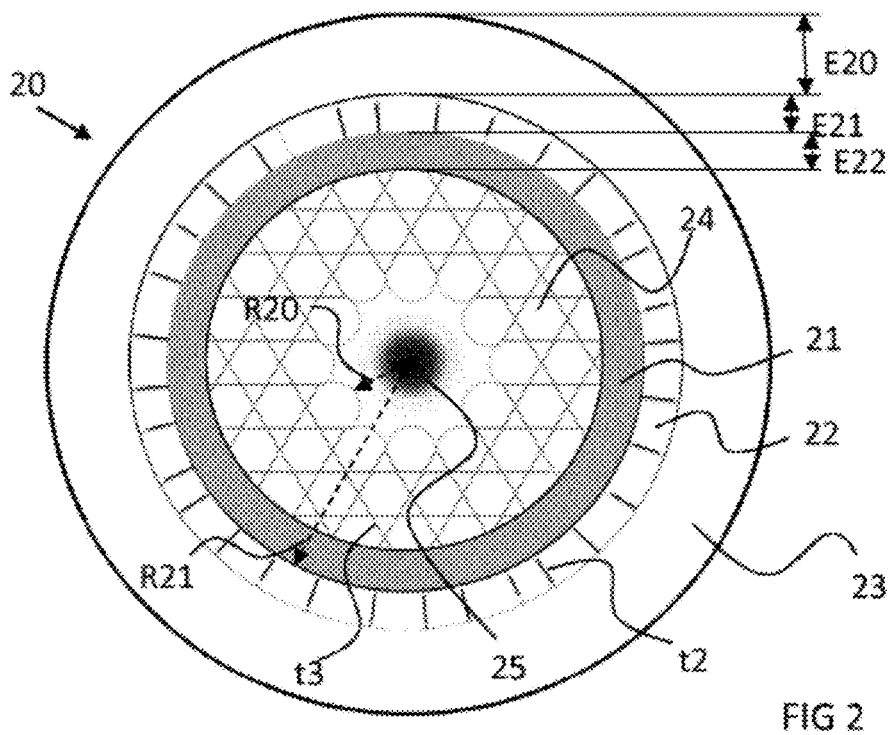
FIG. 2 represents a second embodiment of the optical fibre according to the invention.
Figure 7:
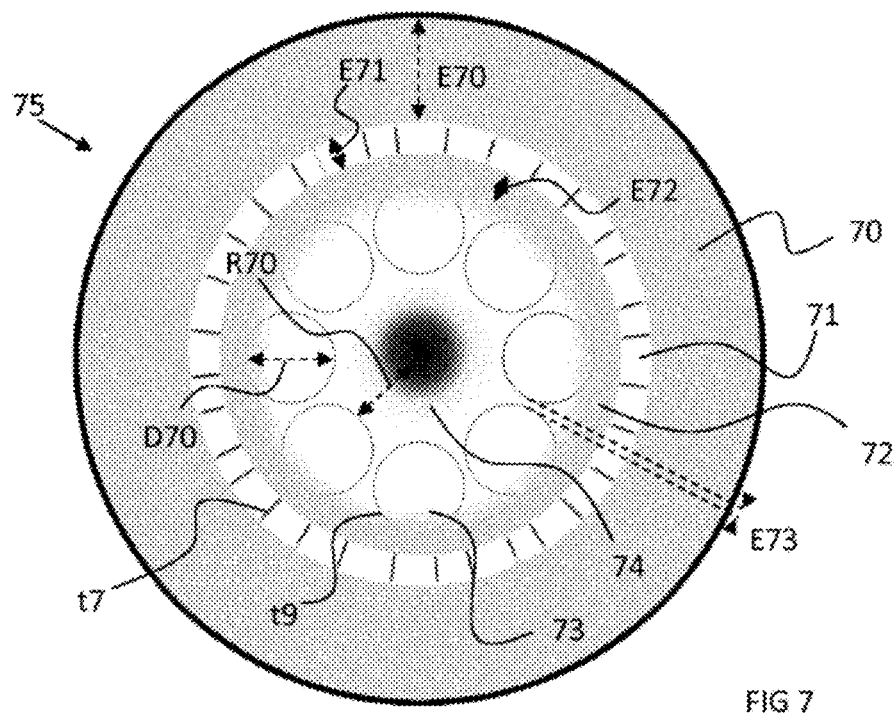
FIG. 7 represents a seventh embodiment of the optical fibre according to the invention.

Characteristics Common to FIGS. 2 and 7

In the embodiments represented in FIGS. 2 and 7, the optical fibre 20, 75 comprises between the external cladding 23, 70 and the light-conducting peripheral structure 21, 72, a gas cladding 22, 71 having an annular structure, supported by glass bridges t2, t7, extending radially from the exterior of said optical fibre 20, 75, in the direction of the centre of the optical fibre 20, 75. This gas cladding improves the confinement of the optical mode in the centre of the optical fibre and makes it possible to reduce the optical mode overlap.

The glass bridges of the gas cladding can have a thickness comprised between 100 nm and 2000 nm.

The gas cladding 22, 71 makes it possible to create a waveguide approximating an ideal waveguide, i.e. produced from a material having a high refractive index surrounded by a material having a low refractive index.

Advantageously, the gas contained in the gas cladding 22, 71 can have a pressure and a composition identical to the gas situated in the cellular structure 24, 73, or even in the core 25, 74.

The gas cladding 22, 71 has a thickness E21, E71 which can be comprised between 10 µm and 100 µm, and preferentially between 20 µm and 60 µm. Even more preferentially, the thickness E21, E71 of the gas cladding can be of the order of 30 µm.

The gas cladding 22, 71 can be preferentially filled with air having a refractive index 1 for a wavelength of 1 µm.

The glass bridges t2, t7 of the gas cladding 22, 71 can have a thickness of the order of 700 nm.

The glass bridges t2, t7 of the gas cladding 22, 71 can have a refractive index of 1.5 for a wavelength of 1 µm.

Characteristics Specific to FIG. 2

FIG. 2 shows a second optical fibre 20 in which the Kagome structure 24 is in contact with the light-conducting peripheral structure 21.

The light-conducting peripheral structure 21 is in contact with the gas cladding 22. The gas cladding 22 is for example in contact with the to external cladding 23.

Figure 3:
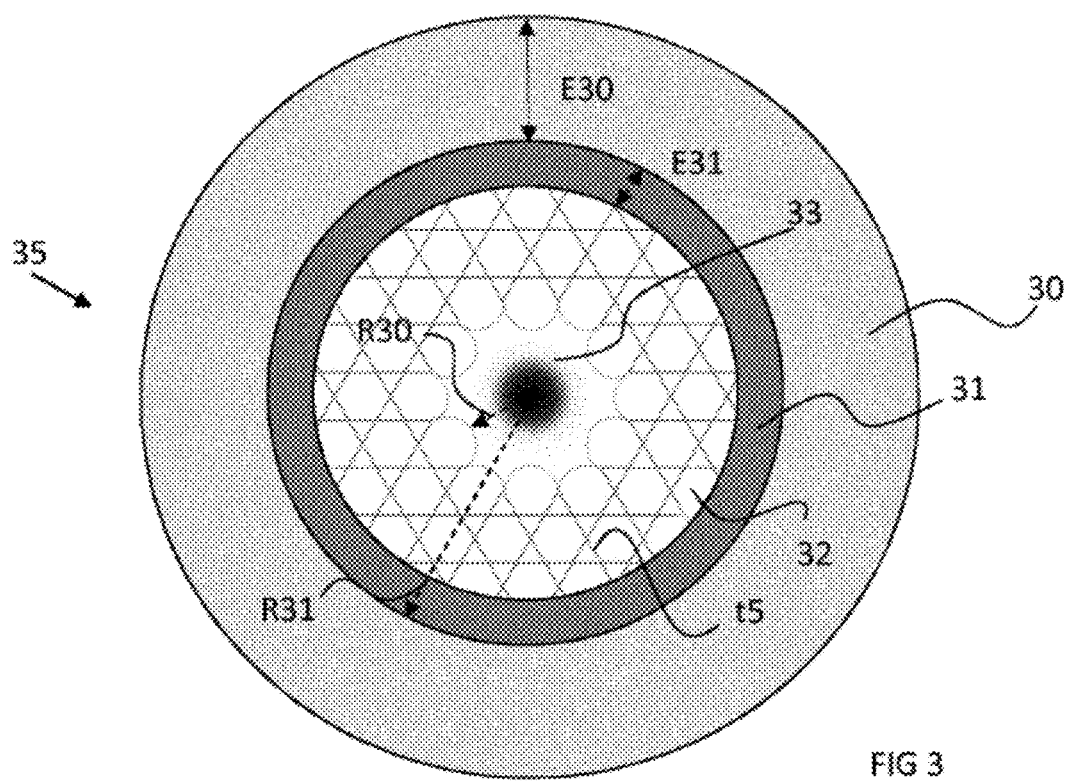
FIG. 3 represents a third embodiment of the optical fibre according to the invention.

Characteristics Specific to FIG. 3

FIG. 3 represents a third optical fibre 35 in which the Kagome structure 32 is in contact with the light-conducting peripheral structure 31.

The light-conducting peripheral structure 31 is in contact with the external cladding 30.

Figure 4:
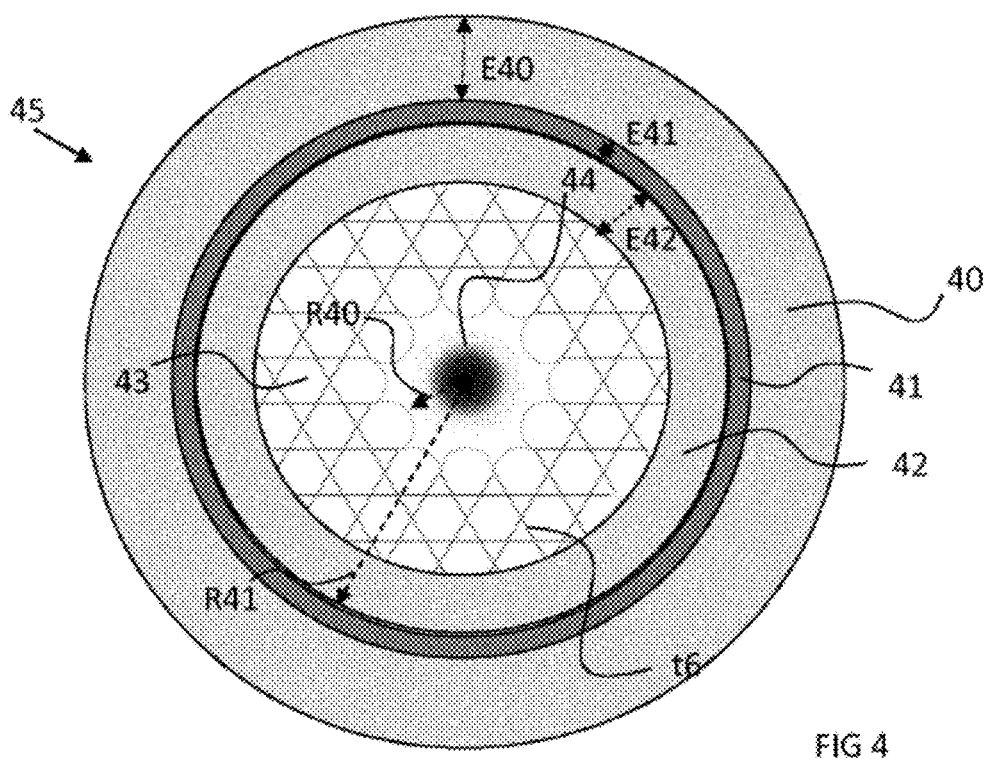
FIG. 4 represents a fourth embodiment of the optical fibre according to the invention.
Figure 6:
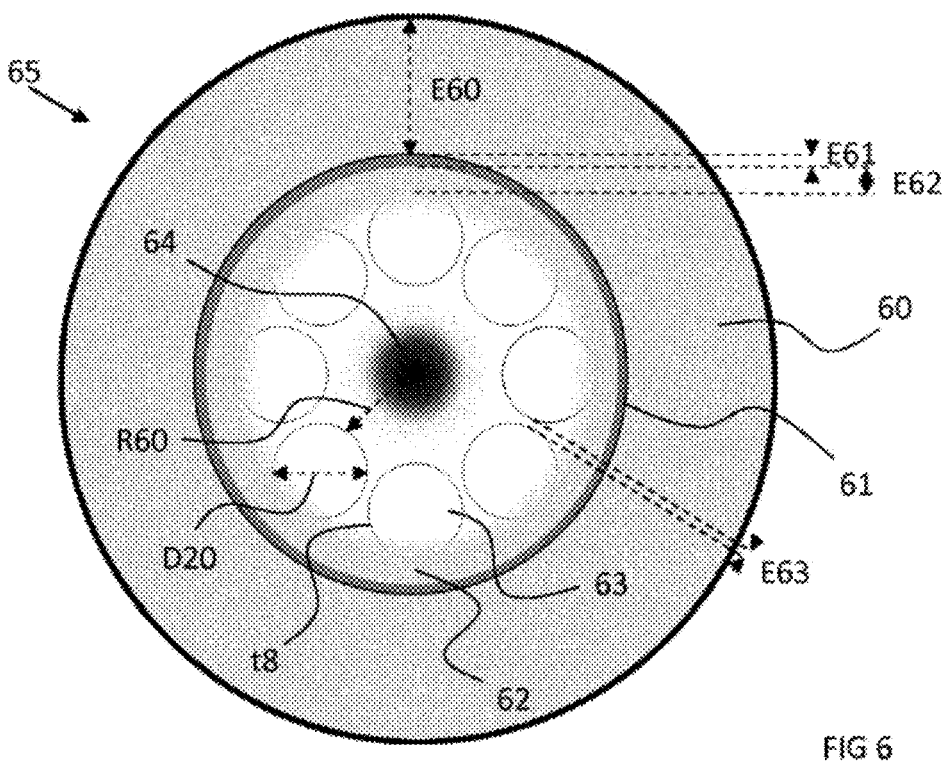
FIG. 6 represents a sixth embodiment of the optical fibre according to the invention.

Characteristics Common to FIGS. 4 and 6

In the embodiments represented in FIGS. 4 and 6, the optical fibre 45, 65 can further comprise an internal cladding 42, 62 between the intermediate layer having a cellular structure 43, 63 and the light-conducting peripheral structure 41, 61.

The internal cladding 42, 62 is in contact with the intermediate layer having a cellular structure 43, 63.

The presence of this internal cladding makes it possible to have one and the same material around the high-index material in order to have a more efficient guiding, i.e. with fewer losses.

The internal cladding 42, 62 can have a thickness E42, E62 comprised between 100 nm and 8 µm and preferentially of the order of 4 µm.

The refractive index of the internal cladding 42, 62 can be 1.45 for a wavelength of 1 µm.

The internal cladding 42, 62 is for example made from the same material as the external cladding 40, 60.

Characteristics Specific to FIG. 4

FIG. 4 diagrammatically represents a fourth optical fibre 45 according to the invention.

In this fourth optical fibre 45, the Kagome structure 43 is in contact with the internal cladding 42.

The internal cladding 42 is in contact with the light-conducting peripheral structure 41.

The light-conducting peripheral structure 41 is in contact with the external cladding 40.

The refractive index of the light-conducting peripheral structure 41 is greater than the refractive index of the internal cladding 42.

Figure 5:
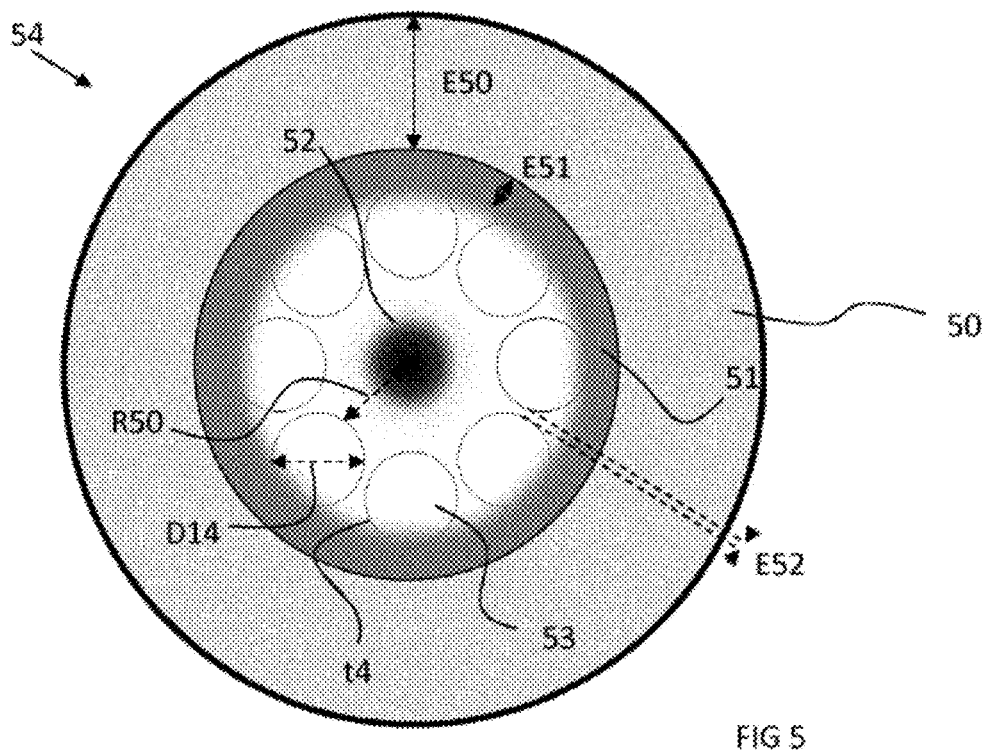
FIG. 5 represents a fifth embodiment of the optical fibre according to the invention.

Characteristics Common to FIGS. 5, 6 and 7

The embodiments of optical fibres 54, 65, 75 according to the invention, represented in FIGS. 5, 6, 7 show an intermediate layer having a cellular structure 53, 63, 73 comprising hollow cylinders at a distance from one another. The hollow cylinders are for example formed by walls or bridges t4, t8, t9 having for example a refractive index of 1.45 for a wavelength of 1 µm.

The hollow cylinders have for example an external diameter D14, D20, D70 comprised between 10 µm and 25 µm, and preferentially of the order of 18 µm. Below these values, guiding by inhibited coupling of the optical fibre is not as effective as the losses are proportional to the perimeter of the cylinders. Above these values, the structure composed of the core and the cylinders d becomes too large to produce monomodal guiding in the core of the fibre.

The walls t4, t8, t9 of the hollow cylinders can have a thickness comprised between 100 nm and 2000 nm.

The walls of the hollow cylinders are for example constituted by silica.

The intermediate layer having a cellular structure 53, 63, 73 preferably comprises a single layer of hollow cylinders.

Guiding by inhibited coupling guiding is supported in the same way by the hollow cylinders as by the Kagome structures of the preceding embodiments. Advantageously, a single ring of unitary cells, i.e. cylinders, is necessary, which considerably reduces the size of the intermediate layer having a cellular structure and thus the bulk of the optical fibre.

The hollow cylinders are at a distance from one another and the interval E52, E63, E73 between two hollow cylinders is comprised between 800 nm and 2 µm and is for example of the order of 800 nm. By interval between two cylinders is meant a distance between two tangents to each cylinder, these two tangents being parallel and as close as possible.

An advantage of the optical fibres 54, 65, 75 comprising hollow cylinders is that the distance between the core 52, 64, 74 guiding by inhibited coupling and the light-conducting peripheral structure 51, 61, 72 is reduced, thus making it possible to collect the fluorescence as close as possible to the high-energy laser radiation.

Characteristics Specific to FIG. 5

FIG. 5 diagrammatically represents a fifth optical fibre 54 in which each hollow cylinder of the layer 53 is in contact with the light-conducting peripheral structure 51.

Each hollow cylinder of the layer 53 is in contact with the core 52. The light-conducting peripheral structure 51 is in contact with the external cladding 50.

Characteristics Specific to FIG. 6

FIG. 6 diagrammatically represents a sixth optical fibre 65 in which each hollow cylinder of the intermediate layer having a cellular structure 63 is in contact with the internal cladding 62.

The internal cladding 62 has for example the same refractive index as the external cladding 60 plus or minus 10%.

Each hollow cylinder of the intermediate layer having a cellular structure 63 is in contact with the core 64.

The internal cladding 62 and the light-conducting peripheral structure 61 are in contact.

The light-conducting peripheral structure 61 and the external cladding 60 are in contact.

Characteristics Specific to FIG. 7

FIG. 7 diagrammatically represents a seventh optical fibre 75 in which each hollow cylinder of the layer 73 is in contact with the light-conducting peripheral structure 72.

The light-conducting peripheral structure 72 is in contact with the gas cladding 71.

The gas cladding 71 is in contact with the external cladding 70.

Each hollow cylinder of the intermediate layer having a cellular structure 73 is in contact with the core 74.

Section on Digital Apertures

Figure 9:
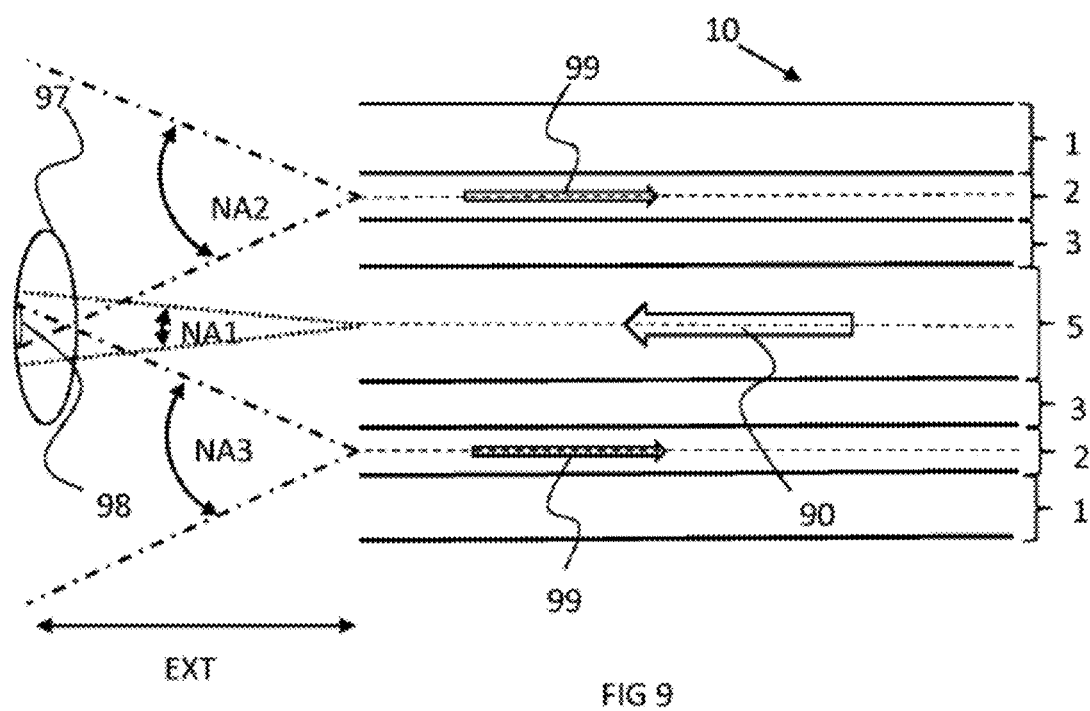
FIG. 9 represents a longitudinal cross section view of the first embodiment of the optical fibre according to the invention.

FIG. 9 represents a cross section view of the first optical fibre 10 as represented in FIG. 1. The optical fibre 10 is represented by way of example, FIG. 9 being able to apply to all the other optical fibres 20, 35, 45, 54, 65, 75 according to the invention.

FIG. 9 shows two different optical paths 90, 99: a first optical path 90 of the high-energy laser beam in the core 5 of the optical fibre 10 in the direction of a target 98, for example a tissue, representing the surface to be ablated. A second optical path 99 represents the collection of the fluorescence 97 from the tissue 98 by the light-conducting peripheral structure 2.

The core 5 as well as the intermediate layer 3 having a cellular structure makes it possible to guide a laser pulse of a duration comprised between 1 ps and 50 fs, and preferentially between 500 fs and 100 fs. The peak power of the pulses can for example be comprised between 1 kW and 10 GW. The laser pulse at the output of the optical fibre 10 diffuses in a first cone the angle NA1 of which defines a first numerical aperture NA1 of the inhibited coupling in the core 5 and of the light-conducting peripheral structure 2. Propagation of light in this type of structure, composed of the core 5 and the light-conducting peripheral structure 2 is close to the single mode and thus has a low numerical aperture. This low numerical aperture is advantageous for applying the high-powered laser flow onto a precise area: the area to be ablated is then only targeted very locally.

In the context of the invention, the first numerical aperture NA1 of the core 5 is defined as less than 0.05 and preferentially between 0.005 and 0.05. The method for manufacturing the optical fibre according to the invention aims to obtain a first numerical aperture NA1 of 0.01.

The laser pulse 90 allows a fluorescence excitation of the tissue is 98. Collection of the fluorescence radiation is carried out by the light-conducting peripheral structure 2. In the example represented in FIG. 9, the light-conducting peripheral structure 2 is composed of blocks 2 which can have a numerical aperture different, for example, between two numerical apertures NA2, NA3 for two blocks that are diametrically opposed. However, in FIG. 9, the two numerical apertures NA2 and NA3 are substantially equal.

In general, the light-conducting peripheral structure 2 allows guiding by total internal reflection the numerical aperture NA2, NA3 of which is much greater, at least ten times, than the first numerical aperture NA1 for collecting a maximum of fluorescence.

In general, to collect a maximum of fluorescence flux, it is necessary to have a numerical aperture that is as large as possible: in fact the fluorescence is a phenomenon in which the propagation of the light takes place by diffusion, i.e. in all directions. The total internal reflection used in the light-conducting peripheral structure 2 makes it possible to obtain a numerical aperture that is advantageously larger.

The propagation of the high-energy laser by inhibited coupling must ensure an optical mode overlap less than $10^{-4}$ and preferentially less than $10^{-5}$ and even more preferentially than $10^{-6}$ The optical mode overlap D is defined as a relationship between the maximum power $P_G$ in the intermediate layer having a cellular structure 3, and the maximum power $P_C$ in the hollow part of the core 5, i.e.:

$$D = \frac{P_G}{P_C}$$

In the case of a Kagome structure 3, in order to ensure that the optical mode overlap is always less than $10^{-4}$, it is necessary to find a compromise between the dimension of the Kagome cells or cylinders, the dimension of the core and the materials used. According to the examples set forth above, such a compromise can be obtained with a dimension of the core 5 and of the Kagome structure 3 or hollow cylinders 53, 63, such that $R_{in}$ is between 15 µm and 60 µm.

The compromise is made taking into account the following constraints: the material (and in particular its refractive index), the rheology during the production of the fibre, the production process, as well as the optical propagation constraints.

With reference to FIG. 9, the numerical apertures of the core 5 and of the light-conducting peripheral structure 2 are such that, at a working distance EXT typically comprised between 100 µm and 10 cm with respect to an end of the fibre 10, there is an intersection between:

any solid angle the vertex of which is a first point of the core 5 at the level of this end and the value of which corresponds to the numerical aperture NA1 of the core at the level of this first point, and any solid angle the vertex of which is a second point of the light-conducting peripheral structure 2 at the level of this end and the value of which corresponds to the numerical aperture NA2 or NA3 of the peripheral structure 2 at the level of this second point.

All of the foregoing in this section on numerical apertures remains valid for all of the embodiments described above:

by replacing the external cladding 1, with the reference 23, 30, 40, 50, 60, or 70, by replacing the light-conducting peripheral structure 2 with the reference 21, 31, 41, 51, 61, or 72, this continuous peripheral structure then only having a single numerical aperture NA2, by replacing the intermediate layer having a cellular structure 3 with the reference 24, 32, 43, 53, 63, or 73, by replacing the hollow core 5, with the reference 25, 33, 44, 52, 64, or 74, by optionally adding (in particular in FIG. 9) one or more of the optional layers 22, 71, 42, 62.

In the present description, all of the numerical apertures are given in air (refractive index 1) at a pressure equal to 1 atmosphere and a temperature of 20° C.

In general and unless otherwise stated, all of the physical to parameters given in the present description are considered at a pressure equal to 1 atmosphere and a temperature of 20° C.

Manufacturing Process

The optical fibre 10, 20, 35, 45, 54, 65, 75 according to the invention is a hollow fibre the terminal ends of which are formed by a ferrule welded to the hollow fibre on one side and a microlens on the other side. The optical fibre according to the invention is manufactured by a method called "stack and draw". An example of this method is described in "Hollow-core photonic bandgap fibre: new light guidance for new science and technology." Philos. Trans. A. Math. Phys. Eng. Sci., vol. 364, no. 1849, pp. 3439-3462, 2006 by F. Benabid.

The welding of the sleeve is carried out conventionally and the lens is manufactured by fusion of the end of a glass rod.

To manufacture the optical fibre 10, 20, 35, 45, 54, 65, 75 according to the invention, glass tubes are drawn down into capillaries, for example, preferentially over a length of 1 m for a diameter of 1 mm for example and preferentially. The capillaries are then stacked to form a stack or bundle of capillaries. The bundle of capillaries is then drawn down preferentially into a cane preform or directly into fibre. The cane is then preferentially sleeved with a glass tube and drawn down to an optical fibre according to a standard method of fibre drawing. During the drawing, the external cladding part, core and interface between the cane and the sleeve are pressurized for example independently in order to obtain a fine control of the thickness t of the walls and glass bridges and of the elliptical arcs having negative curvature. The pressure values depend on the drawing conditions and the drawing infrastructure.

It is known to compensate for the thinning of the cavities of the Kagome structures, cylinders and the gas cladding by surface tension by pressurizing said cavities. The surface tension depends both on the geometry of the cavities (curvature and thickness) and on the parameters of drawing (temperature and drawing speed) and of the oven used (size of the heating area).

To produce the first optical fibre 10 according to the invention and in particular the blocks 2, other glass bars are drawn and arranged in the bundle of capillaries during the stacking operation. Alternatively, it is also possible to add the blocks 2 during the drawing operation by intercalating the other bars between the cane and the sleeve.

To produce the second optical fibre 20 it is necessary to form the light-conducting peripheral structure 21 and the gas cladding 22. The ring of the light-conducting peripheral structure 21 can be added during the sleeving of the cane. With regard to the gas cladding 22, it can be formed by very fine glass tubes, at least as fine as the thickness of the capillaries. The glass tubes are intercalated between the bars of the cane and the sleeve.

To produce the high-index cladding or light-conducting peripheral structure 31 of the third optical fibre 35, capillaries made from germanium-doped silica are added during the stacking operation. The silica capillaries are sufficiently close to fuse and create a continuous cladding.

To produce the internal cladding 42 of the fourth optical fibre 45, it is possible to proceed as for the high-index light-conducting peripheral structure 21: low-index capillaries are added at the time of formation of the stack. The capillaries are sufficiently close to fuse and create a continuous structure.

With regard to the ring of the light-conducting peripheral structure 51, 61 of the fifth and sixth optical fibres 54, 65, it can be produced by sleeving a high-index glass tube, for example made from doped silica, in another low-index glass tube, for example made from pure silica. The assembly can then be drawn into a glass tube which will be used as a sleeve for the stack of capillaries. Alternatively, the ring of the conductive peripheral structure 51, 61 can be produced by intercalating a high-index tube between the preformed cane and its sleeve.

To produce the seventh optical fibre 75 according to the invention, the methods for producing the second optical fibre 20 and the methods used to produce the fifth and sixth optical fibres 54, 65 are used.

Of course, the invention is not limited to the examples that have to just been described, and numerous modifications may be made to these examples without exceeding the scope of the invention.

For example, the bridges are not necessarily made from glass.

For example, it is also possible to adapt an optical element such as a lens, a plane surface, a prism or another optical element, to a terminal end of the optical fibre thus making it possible to confine the gas in the fibre while providing additional optical functions.

Advantageously, the invention allows guiding by inhibited coupling and total internal reflection in one and the same optical fibre, which thus makes it possible to have a multiphoton microscopy endoscope instrument integrating such an optical fibre, in particular in vitro.

The invention claimed is:

1. An optical fibre comprising:
    a hollow core the periphery of which has an order of symmetry of at least six when considering axes of symmetry passing through the centre of the core and through the centre of convex shapes, seen from the centre of the core, said convex shapes at least partially composing the periphery of the core, the periphery of the core has a shape resulting from a combination of elliptical arcs that are convex seen from the centre of the core;
    an intermediate layer having a cellular structure surrounding the core, said intermediate layer having a cellular structure having walls the thickness of which is comprised between 100 nm and 2000 nm, the cellular structure being a Kagome structure, the combination of elliptical arcs constituting a boundary between the Kagome structure and the core;
    a light-conducting peripheral structure surrounding the intermediate layer having a cellular structure; and
    an external cladding surrounding the light-conducting peripheral structure.

2. The optical fibre according to claim 1, characterized in that the intermediate layer having a cellular structure has a thickness comprised between 10 μm and 75 μm.

3. The optical fibre according to claim 1, characterized in that the light-conducting peripheral structure has a thickness comprised between 1 μm and 10 μm.

4. The optical fibre according to claim 1, characterized in that the minimum radius of the periphery of the core is comprised between 20 μm and 60 μm.

5. The optical fibre according to claim 1, characterized in that the light-conducting peripheral structure has a refractive index greater than that of the external cladding.

6. The optical fibre according to claim 1, characterized in that the light-conducting peripheral structure has a numerical aperture greater than 0.1.

7. The optical fibre according to claim 1, characterized in that the light-conducting peripheral structure, is a continuous annular peripheral structure having a thickness comprised between 2 μm and 8 μm.

8. The optical fibre according to claim 1, characterized in that the elliptical arcs are parameterized by a coefficient $b=d/r$, where d is a first radius of the ellipse directed towards the centre of the core and r is a second radius of the ellipse substantially perpendicular to d, b being comprised between 0.4 and 1.5.

9. The optical fibre according to claim 1, characterized in that the combination of elliptical arcs comprises alternately a first elliptical arc the smallest distance to the centre of the core of which is a radius $R_{in}$, and a second elliptical arc the smallest distance to the centre of the core of which is a radius $R_{out}$, with $R_{in}/R_{out}$ comprised between 0.6 and 0.9.

10. The optical fibre according to claim 1, characterized in that the Kagome structure has a thickness comprised between at least one element having Kagome structure and four elements having Kagome structure, a Kagome structure element having a diameter comprised between 10 μm and 25 μm.

11. The optical fibre according to claim 1, characterized in that each element of the Kagome structure is delimited by a set of walls called bridges, said bridges have a refractive index less than that of the external cladding or substantially equal to that of the external cladding to plus or minus 10%.

12. The optical fibre according to claim 11, characterized in that the bridges of the Kagome structure have a thickness comprised between $\lambda_c/2.6$ and $\lambda_c/2.8$, $\lambda_c$ being a wavelength to be guided.

13. The optical fibre according to claim 1, characterized in that the light-conducting peripheral structure comprises blocks the thickness of which is greater than the thickness of the bridges of the Kagome structure and the refractive index of which is greater than the refractive index of the external cladding, said blocks being situated between the Kagome structure and the external cladding.

14. The optical fibre according to claim 1, characterized in that it comprises, between the external cladding and the light-conducting peripheral structure, a gas cladding having an annular structure, supported by glass bridges, extending radially from the exterior of said optical fibre in the direction of the centre of the optical fibre.

15. The optical fibre according to claim 14, characterized in that the bridges of the gas cladding have a thickness comprised between 100 nm and 2000 nm.

16. The optical fibre according to claim 14, characterized in that the Kagome structure is in contact with the light-conducting peripheral structure, itself in contact with the gas cladding which is itself in contact with the external cladding.

17. The optical fibre according to claim 14, further including a plurality of hollow cylinders and characterized in that each of the hollow cylinders is in contact with the light-conducting peripheral structure, itself in contact with the gas cladding, said gas cladding being in contact with the external cladding.

18. The optical fibre according to claim 1, characterized in that the intermediate layer having a cellular structure comprises a single layer of hollow cylinders made from dielectric material at a distance from one another.

19. The optical fibre according to claim 18, characterized in that the walls of the hollow cylinders have a thickness comprised between 100 nm and 2000 nm.

20. The optical fibre according to claim 18, characterized in that each hollow cylinder is in contact with the light-conducting peripheral structure or the internal cladding.

21. An optical fibre comprising:
   a hollow core the periphery of which has an order of symmetry of at least six when considering axes of symmetry passing through the centre of the core and through the centre of convex shapes, seen from the centre of the core, said convex shapes at least partially composing the periphery of the core;
   an intermediate layer having a cellular structure surrounding the core, said intermediate layer having a cellular structure having walls the thickness of which is comprised between 100 nm and 2000 nm;
   a light-conducting peripheral structure surrounding the intermediate layer having a cellular structure;
   an external cladding surrounding the light-conducting peripheral structure; and
   an internal cladding between the intermediate layer having a cellular structure and the light-conducting peripheral structure, the internal cladding being in contact with the intermediate layer that has a cellular structure.

22. The optical fibre according to claim 21, characterized in that the internal cladding is in contact with the light-conducting peripheral structure, said light-conducting peripheral structure being in contact with the external cladding.

23. The optical fibre according to claim 14, characterized in that the internal cladding has a thickness comprised between 100 nm and 8 µm.

24. The optical fibre according to claim 21, characterized in that the intermediate layer having a cellular structure has a thickness comprised between 10 µm and 75 µm.

25. The optical fibre according to claim 21, characterized in that the light-conducting peripheral structure has a thickness comprised between 1 µm and 10 µm.

26. The optical fibre according to claim 21, characterized in that the minimum radius of the periphery of the core is comprised between 20 µm and 60 µm.

27. The optical fibre according to claim 21, characterized in that the light-conducting peripheral structure has a refractive index greater than that of the external cladding.

28. The optical fibre according to claim 21, characterized in that the light-conducting peripheral structure has a numerical aperture greater than 0.1.

29. The optical fibre according to claim 21, characterized in that the light-conducting peripheral structure, is a continuous annular peripheral structure having a thickness comprised between 2 µm and 8 µm.

* * * * *